(12) United States Patent
Tung

(10) Patent No.: US 6,712,612 B1
(45) Date of Patent: Mar. 30, 2004

(54) SAFE AND STABLE RETROVIRAL HELPER CELL LINE AND RELATED COMPOSITIONS AND METHODS

(75) Inventor: Frank Yao Tsung Tung, Duluth, GA (US)

(73) Assignee: GeneCure LLC, Atlanta, GA (US)

( * ) Notice: Subject to any disclaimer, the term of this patent is extended or adjusted under 35 U.S.C. 154(b) by 138 days.

(21) Appl. No.: 10/020,669

(22) Filed: Dec. 12, 2001

Related U.S. Application Data
(60) Provisional application No. 60/255,231, filed on Dec. 12, 2000.

(51) Int. Cl.[7] .......................... C12P 21/06; C12Q 1/70; C07H 21/04; A61K 39/12; A61K 39/21
(52) U.S. Cl. ................... 434/69.1; 435/5; 336/23.72; 424/199.1; 424/208.1
(58) Field of Search ............... 435/69.1, 5; 536/23.72; 424/199.1, 208.1

(56) References Cited

U.S. PATENT DOCUMENTS

| | | |
|---|---|---|
| 5,665,577 A | 9/1997 | Sodroski et al. |
| 5,686,279 A | 11/1997 | Finer et al. |
| 5,994,136 A | 11/1999 | Naldini et al. |
| 6,013,516 A | 1/2000 | Verma et al. |
| 6,165,782 A | 12/2000 | Naldini et al. |
| 6,207,455 B1 | 3/2001 | Chang |

FOREIGN PATENT DOCUMENTS

| | | |
|---|---|---|
| WO | WO 97/12622 | 4/1997 |
| WO | WO 98/17816 | 4/1998 |
| WO | WO 98/39463 | 9/1998 |
| WO | WO 98/51810 | 11/1998 |
| WO | WO 99/04026 | 1/1999 |
| WO | WO 99/15641 | 4/1999 |
| WO | WO 99/30742 | 6/1999 |
| WO | WO 99/31251 | 6/1999 |
| WO | WO 99/32646 | 7/1999 |

OTHER PUBLICATIONS

*AIDS Research and Human Retroviruses*, vol. 6, No. 11, 1990, "The Complete Nucleotide Sequence of a Pathogenic Molecular Clone of Simian Immunodifiency Virus" Regier, Dean A. and Desrosiers, Ronald C.
GenBank Accession No. M33262.

*Primary Examiner*—Hankyel T. Park
(74) *Attorney, Agent, or Firm*—Kirkpatrick & Lockhart LLP

(57) ABSTRACT

A safe gene transfer system is provided based on simian immunodeficiency virus (SIV). A packaging construct is provided in which the SIV packaging sequence is removed, and, in one instance, the gag, pol and other accessory genes are expressed under the control of CMV promoter. SIV transfer constructs are provided in which cis-acting sequences required for viral replication (R, tRNA primer binding site, encapsidation site, RRE sequence and 3' LTR), with or without a marker gene, are described. Stable packaging cell lines are provided that were prepared by transfecting 293(T) cells with an SIV packaging construct. High titer virus (>$10^7$ transducing units/ml) can be produced upon transient transfection with SIV transfer vectors. The safety of the described SIV gene transfer vectors was further tested in a primate model. Rhesus monkeys that received multiple inoculations of high titer ($10^7$) retroviral vectors did not develop any signs of side effects.

71 Claims, 5 Drawing Sheets

Fig. 2A

```
                                          initiation of translation
sd                                                    ↓
caacacaaaaaagaaatagctgtcttttatccaggaaggggtaataagatagagtgggagATG
``` sd: splicing donor site

Fig. 2B

```
     740                760                      780
SIV       GATGTATAAATATCACTGCATTTCGCTCTGTATTCAGTCGCTCTG
          ↑TATA box                           ↳ R
```

CMV    aggtctatataagcagagctctctggctaactagagaacccactgcttactggcttatcg
       ↑ TATA box            ↳ transcription start pCRLacZ    aggtctatataagcagagctctctCTCTGTATTCAGTCGCTCTG
           ↑ TATA box            ↳ transcription start  R

SEQUENCE LISTING

<160> NUMBER OF SEQ ID NOS: 17

<210> SEQ ID NO 1
<211> LENGTH: 63
<212> TYPE: DNA
<213> ORGANISM: Artificial Sequence
<220> FEATURE:
<223> OTHER INFORMATION: SIV packaging sequence
<221> NAME/KEY: misc_feature
<222> LOCATION: (9)..(48)

<223> OTHER INFORMATION: Deleted Packaging Sequence

<400> SEQUENCE: 1

```
caacacaaaa aagaaatagc tgtcttttat ccaggaaggg gtaataagat agagtgggag    60
atg                                                                 63
```

<210> SEQ ID NO 2
<211> LENGTH: 45
<212> TYPE: DNA
<213> ORGANISM: Simian immunodeficiency virus

<400> SEQUENCE: 2

```
gatgtataaa tatcactgca tttcgctctg tattcagtcg ctctg                   45
```

<210> SEQ ID NO 3
<211> LENGTH: 60
<212> TYPE: DNA
<213> ORGANISM: Human cytomegalovirus

<400> SEQUENCE: 3

```
aggtctatat aagcagagct ctctggctaa ctagagaacc cactgcttac tggcttatcg    60
```

<210> SEQ ID NO 4
<211> LENGTH: 44
<212> TYPE: DNA
<213> ORGANISM: Artificial Sequence
<220> FEATURE:
<223> OTHER INFORMATION: pCRLacZ CMV/initiator fusion

<400> SEQUENCE: 4

```
aggtctatat aagcagagct ctctctctgt attcagtcgc tctg                    44
```

<210> SEQ ID NO 5
<211> LENGTH: 10535
<212> TYPE: DNA
<213> ORGANISM: Simian immunodeficiency virus

<400> SEQUENCE: 5

```
gcatgcacat tttaaaggct tttgctaaat atagccaaaa gtccttctac aaattttcta    60
agagttctga ttcaaagcag taacaggcct tgtctcatca tgaactttgg catttcatct   120
acagctaagt ttatatcata aatagttctt tacaggcagc accaacttat acccttatag   180
catactttac tgtgtgaaaa ttgcatcttt cattaagctt actgtaaatt tactggctgt   240
cttccttgca ggtttctgga agggatttat tacagtgcaa gaagacatag aatcttagac   300
atatacttag aaaaggaaga aggcatcata ccagattggc aggattacac ctcaggacca   360
ggaattagat acccaaagac atttggctgg ctatggaaat tagtccctgt aaatgtatca   420
gatgaggcac aggaggatga ggagcattat ttaatgcatc cagctcaaac ttcccagtgg   480
gatgaccctt ggggagaggt tctagcatgg aagtttgatc caactctggc ctacacttat   540
gaggcatatg ttagataccc agaagagttt ggaagcaagt caggcctgtc agaggaagag   600
gttagaagaa ggctaaccgc aagaggcctt cttaacatgg ctgacaagaa ggaaactcgc   660
tgaaacagca gggactttcc acaagggat gttacgggga ggtactgggg aggagccggt   720
cgggaacgcc cactttcttg atgtataaat atcactgcat ttcgctctgt attcagtcgc   780
tctgcggaga ggctggcaga ttgagccctg ggaggttctc tccagcacta gcaggtagag   840
cctgggtgtt ccctgctaga ctctcaccag cacttggccg gtgctgggca gagtgactcc   900
acgcttgctt gcttaaagcc ctcttcaata aagctgccat tttagaagta agctagtgtg   960
```

```
tgttcccatc tctcctagcc gccgcctggt caactcggta ctcaataata agaagaccct    1020
ggtctgttag gaccctttct gctttgggaa accgaagcag gaaaatccct agcagattgg    1080
cgcctgaaca gggacttgaa ggagagtgag agactcctga gtacggctga gtgaaggcag    1140
taagggcggc aggaaccaac cacgacggag tgctcctata aaggcgcggg tcggtaccag    1200
acggcgtgag gagcgggaga ggaagaggcc tccggttgca ggtaagtgca acacaaaaaa    1260
gaaatagctg tcttttatcc aggaaggggt aataagatag agtgggagat gggcgtgaga    1320
aactccgtct tgtcagggaa gaaagcagat gaattagaaa aaattaggct acgacccaac    1380
ggaaagaaaa agtacatgtt gaagcatgta gtatgggcag caaatgaatt agatagattt    1440
ggattagcag aaagcctgtt ggagaacaaa gaaggatgtc aaaaaatact ttcggtctta    1500
gctccattag tgccaacagg ctcagaaaat ttaaaaagcc tttataatac tgtctgcgtc    1560
atctggtgca ttcacgcaga agagaaagtg aaacacactg aggaagcaaa acagatagtg    1620
cagagacacc tagtggtgga acaggaaca acagaaacta tgccaaaaac aagtagacca    1680
acagcaccat ctagcggcag aggaggaaat tacccagtac aacaaatagg tggtaactat    1740
gtccacctgc cattaagccc gagaacatta aatgcctggg taaaattgat agaggaaaag    1800
aaatttggag cagaagtagt gccaggattt caggcactgt cagaaggttg cacccctat    1860 gacattaatc agatgttaaa ttgtgtggga gaccatcaag cggctatgca gattatcaga    1920
gatattataa acgaggaggc tgcagattgg gacttgcagc acccacaacc agctccacaa    1980
caaggacaac ttagggagcc gtcaggatca gatattgcag gaacaactag ttcagtagat    2040
gaacaaatcc agtggatgta cagacaacag aaccccatac cagtaggcaa catttacagg    2100
agatggatcc aactggggtt gcaaaaatgt gtcagaatgt ataacccaac aaacattcta    2160
gatgtaaaac aaggggccaaa agagccattt cagagctatg tagacaggtt ctacaaaagt    2220
ttaagagcag aacagacaga tgcagcagta aagaattgga tgactcaaac actgctgatt    2280
caaaatgcta acccagattg caagctagtg ctgaaggggc tgggtgtgaa tcccacccta    2340
gaagaaatgc tgacggcttg tcaaggagta gggggggccgg gacagaaggc tagattaatg    2400
gcagaagccc tgaaagaggc cctcgcacca gtgccaatcc cttttgcagc agcccaacag    2460
aggggaccaa gaaagccaat taagtgttgg aattgtggga agagggaca ctctgcaagg    2520 caatgcagag ccccaagaag acagggatgc tggaaatgtg gaaaaatgga ccatgttatg    2580
gccaaatgcc cagacagaca ggcgggtttt ttaggccttg tccatggggg aaagaagccc    2640
cgcaatttcc ccatggctca agtgcatcag gggctgatgc caactgctcc cccagaggac    2700
ccagctgtgg atctgctaaa gaactacatg cagttgggca agcagcagag agaaaagcag    2760
agagaaagca gagagaagcc ttacaaggag gtgacagagg atttgctgca cctcaattct    2820
ctctttggag gagaccagta gtcactgctc atattgaagg acagcctgta gaagtattac    2880
tggatacagg ggctgatgat tctattgtaa caggaataga gttaggtcca cattataccc    2940
caaaaatagt aggaggaata ggaggttta ttaatactaa agaatacaaa aatgtagaaa    3000
tagaagtttt aggcaaaagg attaagggga caatcatgac aggggacacc ccgattaaca    3060
tttttggtag aaatttgcta acagctctgg ggatgtctct aaattttccc atagctaaag    3120
tagagcctgt aaaagtcgcc ttaaagccag gaaaggatgg accaaaattg aagcagtggc    3180
cattatcaaa agaaaagata gttgcattaa gagaaatctg tgaaaagatg gaaaaggatg    3240
gtcagttgga ggaagctccc ccgaccaatc catacaacac ccccacattt gctataaaga    3300
```

-continued

```
aaaaggataa gaacaaatgg agaatgctga tagattttag ggaactaaat agggtcactc   3360
aggactttac ggaagtccaa ttaggaatac cacaccctgc aggactagca aaaaggaaaa   3420
gaattacagt actggatata ggtgatgcat atttctccat acctctagat gaagaattta   3480
ggcagtacac tgcctttact ttaccatcag taaataatgc agagccagga aaacgataca   3540
tttataaggt tctgcctcag ggatggaagg ggtcaccagc catcttccaa tacactatga   3600
gacatgtgct agaaccttc aggaaggcaa atccagatgt gaccttagtc cagtatatgg   3660
atgacatctt aatagctagt gacaggacag acctggaaca tgacagggta gttttacagt   3720
caaaggaact cttgaatagc atagggtttt ctaccccaga gagaaattc caaaaagatc   3780 ccccatttca atggatgggg tacgaattgt ggccaacaaa atggaagttg caaaagatag   3840
agttgccaca aagagagacc tggacagtga atgatataca gaagttagta ggagtattaa   3900
attgggcagc tcaaattat ccaggtataa aaccaaaca tctctgtagg ttaattagag   3960
gaaaaatgac tctaacagag gaagttcagt ggactgagat ggcagaagca gaatatgagg   4020
aaaataaaat aattctcagt caggaacaag aaggatgtta ttaccaagaa ggcaagccat   4080
tagaagccac ggtaataaag agtcaggaca atcagtggtc ttataaaatt caccaagaag   4140
acaaaatact gaaagtagga aaatttgcaa agataaagaa tacacatacc aatggagtga   4200
gactattagc acatgtaata cagaaaatag gaaaggaagc aatagtgatc tggggacagg   4260
tcccaaaatt ccacttacca gttgagaagg atgtatggga acagtggtgg acagactatt   4320
ggcaggtaac ctggataccg gaatgggatt ttatctcaac accaccgcta gtaagattag   4380
tcttcaatct agtgaaggac cctatagagg gagaagaaac ctattataca gatgatcat   4440 gtaataaaca gtcaaaagaa gggaaagcag gatatatcac agatagggc aaagacaaag   4500 taaaagtgtt agaacagact actaatcaac aagcagaatt ggaagcattt ctcatggcat   4560
tgacagactc agggccaaag gcaaatatta tagtagattc acaatatgtt atgggaataa   4620
taacaggatg ccctacagaa tcagagagca ggctagttaa tcaaataata gaagaaatga   4680
ttaaaaagtc agaaatttat gtagcatggg taccagcaca caaaggtata ggaggaaacc   4740
aagaaataga ccacctagtt agtcaaggga ttagacaagt tctcttcttg gaaaagatag   4800
agccagcaca agaagaacat gataaatacc atagtaatgt aaaagaattg gtattcaaat   4860
ttggattacc cagaatagtg gccagacaga tagtagacac ctgtgataaa tgtcatcaga   4920
aaggagaggc tatacatggg caggcaaatt cagatctagg gacttggcaa atggattgta   4980
cccatctaga gggaaaaata atcatagttg cagtacatgt agctagtgga ttcatagaag   5040
cagaggtaat tccacaagag acaggaagac agacagcact atttctgtta aaattggcag   5100
gcagatggcc tattacacat ctacacacag ataatggtgc taactttgct tcgcaagaag   5160
taaagatggt tgcatggtgg gcagggtag agcacacctt tggggtacca tacaatccac   5220
agagtcaggg agtagtggaa gcaatgaatc accacctgaa aaatcaaata gatagaatca   5280
gggaacaagc aaattcagta gaaaccatag tattaatggc agttcattgc atgaatttta   5340
aaagaagggg aggaataggg gatatgactc cagcagaaag attaattaac atgatcacta   5400
cagaacaaga gatacaattt caacaatcaa aaaactcaaa attaaaaat tttcgggtct   5460 attacagaga aggcagagat caactgtgga agggaccgg tgagctattg tggaaagggg   5520
aaggagcagt catcttaaag gtagggcag acattaaggt agtacccaga agaaaggcta   5580
aaattatcaa agattatgga ggaggaaaag aggtggatag cagttccac atggaggata   5640 ccggagaggc tagagaggtg gcatagcctc ataaaatatc tgaaatataa aactaaagat   5700
```

-continued

```
ctacaaaagg tttgctatgt gccccatttt aaggtcggat gggcatggtg gacctgcagc    5760
agagtaatct tcccactaca ggaaggaagc catttagaag tacaagggta ttggcatttg    5820
acaccagaaa aagggtggct cagtacttat gcagtgagga taacctggta ctcaaagaac    5880
ttttggacag atgtaacacc aaactatgca gacattttac tgcatagcac ttatttccct    5940
tgctttacag cgggagaagt gagaagggcc atcagggaga acaactgct gtcttgctgc     6000 aggttcccga gagctcataa gtaccaggta ccaagcctac agtacttagc actgaaagta    6060
gtaagcgatg tcagatccca gggagagaat cccacctgga acagtggag aagagacaat     6120 aggagaggcc ttcgaatggc taaacagaac agtagaggag ataaacagag aggcggtaaa    6180
ccacctacca agggagctaa ttttccaggt ttggcaaagg tcttgggaat actggcatga    6240
tgaacaaggg atgtcaccaa gctatgtaaa atacagatac ttgtgtttaa tacaaaaggc    6300
tttatttatg cattgcaaga aaggctgtag atgtctaggg gaaggacatg gggcagggg     6360 atggagacca ggacctcctc ctcctccccc tccaggacta gcataaatgg aagaaagacc    6420
tccagaaaat gaaggaccac aaagggaacc atgggatgaa tgggtagtgg aggttctgga    6480
agaactgaaa gaagaagctt taaaacattt tgatcctcgc ttgctaactg cacttggtaa    6540
tcatatctat aatagacatg gagacaccct tgagggagcg ggagaactca ttagaatcct    6600
ccaacgagcg ctcttcatgc atttcagagg cggatgcatc cactccagaa tcggccaacc    6660
tgggggagga atcctctct cagctatacc gccctctaga agcatgctat aacacatgct     6720
attgtaaaaa gtgttgctac cattgccagt tttgttttct taaaaaaggc ttggggatat    6780
gttatgagca atcacgaaag agaagaagaa ctccgaaaaa ggctaaggct aatacatctt    6840
ctgcatcaaa caagtaagta tgggatgtct tgggaatcag ctgcttatcg ccatcttgct    6900
tttaagtgtc tatgggatct attgtactct atatgtcaca gtcttttatg gtgtaccagc    6960
ttggaggaat gcgacaattc ccctcttttg tgcaaccaag aatagggata cttggggaac    7020
aactcagtgc ctaccagata atggtgatta ttcagaagtg gcccttaatg ttacagaaag    7080
ctttgatgcc tggaataata cagtcacaga acaggcaata gaggatgtat ggcaactctt    7140
tgagacctca ataaagcctt gtgtaaaatt atccccatta tgcattacta tgagatgcaa    7200
taaaagtgag acagatagat ggggattgac aaaatcaata acaacaacag catcaacaac    7260
atcaacgaca gcatcagcaa aagtagacat ggtcaatgag actagttctt gtatagccca    7320
ggataattgc acaggcttgg aacaagagca aatgataagc tgtaaattca acatgacagg    7380
gttaaaaaga gacaagaaaa aagagtacaa tgaaacttgg tactctgcag atttggtatg    7440
tgaacaaggg aataacactg gtaatgaaag tagatgttac atgaaccact gtaacacttc    7500
tgttatccaa gagtcttgtg acaaacatta ttgggatgct attagattta ggtattgtgc    7560
acctccaggt tatgctttgc ttagatgtaa tgacacaaat tattcaggct ttatgcctaa    7620
atgttctaag gtggtggtct cttcatgcac aaggatgatg gagacacaga cttctacttg    7680
gtttggcttt aatggaacta gagcagaaaa tagaacttat atttactggc atggtaggga    7740
taataggact ataattagtt taaataagta ttataatcta acaatgaaat gtagaagacc    7800
aggaaataag acagttttac cagtcaccat tatgtctgga ttggttttcc actcacaacc    7860
aatcaatgat aggccaaagc aggcatggtg ttggtttgga ggaaaatgga aggatgcaat    7920
aaaagaggtg aagcagacca ttgtcaaaca tcccaggtat actggaacta acaatactga    7980
taaaatcaat ttgacggctc ctgaggagg agatccggaa gttaccttca tgtggacaaa    8040
```

-continued

```
ttgcagagga gagttcctct actgtaaaat gaattggttt ctaaattggg tagaagatag    8100
gaatacagct aaccagaagc caaaggaaca gcataaaagg aattacgtgc catgtcatat    8160
tagacaaata atcaacactt ggcataaagt aggcaaaaat gtttatttgc ctccaagaga    8220
gggagacctc acgtgtaact ccacagtgac cagtctcata gcaaacatag attggattga    8280
tggaaaccaa actaatatca ccatgagtgc agaggtggca gaactgtatc gattggaatt    8340
gggagattat aaattagtag agatcactcc aattggcttg cccccacag atgtgaagag     8400
gtacactact ggtggcacct caagaaataa agaggggtc tttgtgctag ggttcttggg     8460
ttttctcgca acggcaggtt ctgcaatggg cgcggcgtcg ttgacgctga ccgctcagtc    8520
ccgaacttta ttggctggga tagtgcagca acagcaacag ctgttggacg tggtcaagag    8580
acaacaagaa ttgttgcgac tgaccgtctg gggaacaaag aacctccaga ctagggtcac    8640
tgccatcgag aagtacttaa aggaccaggc gcagctgaat gcttggggat gtgcgtttag    8700
acaagtctgc cacactactg taccatggcc aaatgcaagt ctaacaccaa agtggaacaa    8760
tgagacttgg caagagtggg agcgaaaggt tgacttcttg gaagaaaata taacagccct    8820
cctagaggag gcacaaattc aacaagagaa gaacatgtat gaattacaaa agttgaatag    8880
ctgggatgtg tttggcaatt ggtttgacct tgcttcttgg ataaagtata tacaatatgg    8940
agtttatata gttgtaggag taatactgtt aagaatagta atctatatag tacaaatgct    9000
agctaagtta aggcagggt ataggccagt gttctcttcc ccaccctctt atttccagca     9060
gacccatatc caacaggacc cggcactgcc aaccagagaa ggcaaagaaa gagacggtgg    9120
agaaggcggt ggcaacagct cctggccttg gcagatagaa tatattcatt tcctgatccg    9180
ccaactgata cgcctcttga cttggctatt cagcaactgc agaaccttgc tatcgagagt    9240
ataccagatc ctccaaccaa tactccagag gctctctgcg accctacaga ggattcgaga    9300
agtcctcagg actgaactga cctacctaca atatgggtgg agctatttcc atgaggcggt    9360
ccaggccgtc tggagatctg cgacagagac tcttgcgggc gcgtggggag acttatggga    9420
gactcttagg agaggtggaa gatggatact cgcaatcccc aggaggatta gacaagggct    9480
tgagctcact ctcttgtgag ggacagaaat acaatcaggg acagtatatg aatactccat    9540
ggagaaaccc agctgaagag agagaaaaat tagcatacag aaaacaaaat atggatgata    9600
tagatgagta agatgatgac ttggtagggg tatcagtgag gccaaaagtt cccctaagaa    9660
caatgagtta caaattggca atagacatgt ctcattttat aaaagaaaag ggggactgg     9720
aagggattta ttacagtgca agaagacata gaatcttaga catatactta gaaaaggaag    9780
aaggcatcat accagattgg caggattaca cctcaggacc aggaattaga tacccaagga    9840
catttggctg gctatggaaa ttagtccctg taaatgtatc agatgaggca caggaggatg    9900
aggagcatta tttaatgcat ccagctcaaa cttcccagtg gatgaccct tggggagagg     9960
ttctagcatg gaagtttgat ccaactctgg cctacactta tgaggcatat gttagatacc   10020
cagaagagtt tggaagcaag tcaggcctgt cagaggaaga ggttagaaga aggctaaccg   10080
caagaggcct tcttaacatg gctgacaaga aggaaactcg ctgaaacagc agggactttc   10140
cacaagggga tgttacgggg aggtactggg gaggagccgg tcgggaacgc ccactttctt   10200
gatgtataaa tatcactgca tttcgctctg tattcagtcg ctctgcggag aggctggcag   10260
attgagccct gggaggttct ctccagcact agcaggtaga gcctgggtgt tccctgctag   10320
actctcacca gcacttggcc ggtgctgggc agagtgactc cacgcttgct tgcttaaagc   10380
cctcttcaat aaagctgcca ttttagaagt aagctagtgt gtgttcccat ctctcctagc   10440
```
cgccgcctgg tcaactcggt actcaataat aagaagaccc tggtctgtta ggacccttc      10500 tgctttggga aaccgaagca ggaaaatccc tagca                                10535

<210> SEQ ID NO 6
<211> LENGTH: 29
<212> TYPE: DNA
<213> ORGANISM: Artificial Sequence
<220> FEATURE:
<223> OTHER INFORMATION: SIV Packaging Sequence Deletion Primer 1

<400> SEQUENCE: 6
aggcgcgcct ttgtgttgca cttacctgc                                       29

<210> SEQ ID NO 7
<211> LENGTH: 28
<212> TYPE: DNA
<213> ORGANISM: Artificial Sequence
<220> FEATURE:
<223> OTHER INFORMATION: SIV Packaging Sequence Deletion Primer 2

<400> SEQUENCE: 7
aggcgcgcct agagtgggag atgggcgt                                        28

<210> SEQ ID NO 8
<211> LENGTH: 27
<212> TYPE: DNA
<213> ORGANISM: Artificial Sequence
<220> FEATURE:
<223> OTHER INFORMATION: SIV Packaging Sequence Deletion Primer 3

<400> SEQUENCE: 8
tttggatcca gtcgctctgc ggagagg                                         27

<210> SEQ ID NO 9
<211> LENGTH: 22
<212> TYPE: DNA
<213> ORGANISM: Artificial Sequence
<220> FEATURE:
<223> OTHER INFORMATION: SIV Packaging Sequence Deletion Primer 4

<400> SEQUENCE: 9
gagacatccc cagagctgtt ag                                              22

<210> SEQ ID NO 10
<211> LENGTH: 31
<212> TYPE: DNA
<213> ORGANISM: Artificial Sequence
<220> FEATURE:
<223> OTHER INFORMATION: Oligonucleotide Primer FT66

<400> SEQUENCE: 10
ttttgcatgc ttcgcgatgt acgggccaga t                                    31

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide Primer FT67

<400> SEQUENCE: 11
agagagctct gcttatatag acct                                            24

<210> SEQ ID NO 12

```
<211> LENGTH: 21
<212> TYPE: DNA
<213> ORGANISM: Artificial Sequence
<220> FEATURE:
<223> OTHER INFORMATION: Oligonucleotide primer FT68

<400> SEQUENCE: 12
ctctgtattc agtcgctctg c                                              21

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide Primer FT28

<400> SEQUENCE: 13
gagacatccc cagagctgtt ag                                             22

<210> SEQ ID NO 14
<211> LENGTH: 21
<212> TYPE: DNA
<213> ORGANISM: Artificial Sequence
<220> FEATURE:
<223> OTHER INFORMATION: U3 Deletion Primer 1

<400> SEQUENCE: 14
gcactgtaat aaatcccttc c                                              21

<210> SEQ ID NO 15
<211> LENGTH: 21
<212> TYPE: DNA
<213> ORGANISM: Artificial Sequence
<220> FEATURE:
<223> OTHER INFORMATION: U3 Deletion Primer 2

<400> SEQUENCE: 15
cactgcattt cgctctgtat t                                              21

<210> SEQ ID NO 16
<211> LENGTH: 27
<212> TYPE: DNA
<213> ORGANISM: Artificial Sequence
<220> FEATURE:
<223> OTHER INFORMATION: Oligonucleotide Primer FT33

<400> SEQUENCE: 16
tttggatcca gtcgctctgc ggagagg                                        27

<210> SEQ ID NO 17
<211> LENGTH: 35
<212> TYPE: DNA
<213> ORGANISM: Artificial Sequence
<220> FEATURE:
<223> OTHER INFORMATION: Oligonucleotide Primer FT34

<400> SEQUENCE: 17
acaagatcta gtttctcacg ccctactccc actct                               35
```

SAFE AND STABLE RETROVIRAL HELPER CELL LINE AND RELATED COMPOSITIONS AND METHODS

RELATED COMPOSITIONS AND METHODS

This Application claims priority under 35 USC §119(e) to U.S. Provisional Patent Application No. 60/255,231 filed Dec. 12, 2000.

BACKGROUND

1. Field of the Invention

Safe and stable packaging cell lines are described for preparing retroviral vectors. Also described are methods of production of therapeutics, vaccines for gene therapy of many genetic and acquired diseases (including AIDS and cancers).

2. Description of the Related Art

Retrovirus is employed as a common tool for stable gene transfer into human cells (See, e.g., Gilboa et al., *BioTechiques* (1986), 4(6): 504–512). The retroviral-mediated gene transfer system can be divided into two components (Miller and Rosman, *BioTechniques* (1989), 7:980–990). This design is based on the knowledge of studying murine retrovirus virus in the early 1980s (Joyner et al., *Nature* (1983), 305: 556–558; Mann et al., *Cell* (1983), 33: 153–159). The first component is the transfer vector itself, which generally include cis-acting sequences required for viral reverse transcription and integration and typically does not encode viral structure proteins. The second component is the retrovirus packaging construct or a cell line (helper cell line), which provides the viral proteins necessary for assembly of viral particles and transduction of recipient cells (Cone and Mulligan, *Proc. Nat'l. Acad. Sci. USA* (1984), 81: 6349–6353). A marker gene or therapeutic gene can be inserted into the transfer vector to be transferred into the recipient cells. Retroviral particles are produced by co-transfecting a transfer vector and a packaging construct into a cell line or by transfecting a transfer vector into a packaging cell line.

One of the potential safety concerns of using retrovirus in humans is the generation of replication-competent retrovirus (RCR) by homologous recombination between transfer vector and packaging construct during co-transfection. The RCR might cause unappreciated harms, such as T cell lymphoma, in the recipients (Danahue et al, *J. Exp. Med.* (1992), 176: 1125–1135). Several approaches have been developed to avoid the generation of RCR. One is to eliminate overlapping sequences between transfer vectors and packaging constructs. Another is to use a packaging cell line instead of co-transfection for viral particle production. Since only a single copy of the packaging sequence typically resides in the packaging cell line, instead of multiple copies in co-transfected cells, the chance to generate RCR is much reduced (Markowitz et al., *J. Virol.* (1988), 62(4): 1120–1124).

The retroviral vectors currently used in clinical gene therapy studies are derived from murine leukemia virus, which has an inherent property of infecting only proliferating cells (Miller et al., *Molecular & Cellular Biology* (1990), 10(8): 4239–42; Lewis and Emerman, *J. Virology* (1994), 68:510–516). Unfortunately, the majority of primary target cells for gene therapy trials are in quiescent stage, which results in low efficiency of gene transduction. Many protocols have been developed to enhance gene transfer efficiency, such as repeated transduction, growth factor stimulation, isolation of progenitor cells and use of high titer pseudotyped virus (Nolta et al., *Exp. Hemotol.* (1992), 20: 1065–1071; Van Beusechem et al., *Gene Therapy* (1995), 2: 245–255; Akina et al., *J. Virology* (1996), 70:22581–2585; Xu et al., *Blood* (1995) 86:141–146). However, the ex vivo manipulation of transduced cells causes the loss of pluripotentiality after engraftment into recipients (Van Beusechem et al., *Gene Therapy* (1995), 2: 245–255). An ideal vector for gene therapy would be able to directly deliver genes into primary cells in the recipients.

To approach this problem, HIV-1 has been developed as a viral vector for gene transfer in nondividing cells (Gallay et al., *J. Virology* (1996), 70: 1027–1032). Gene transfer has been demonstrated in quiescent cells using an HIV-1 based vector (Naldini et al., *Science* (1996), 272:263–267). In vitro, HIV-1 can infect primary cultures of monocyte-derived macrophages as well as cell cycle-arrested $CD4^+$ T lymphoid cells (Strizki et al., *J. Virology* (1996), 70: 7654–62). Stable HIV-1 packaging cell lines have been developed to produce modest titer ($10^{3-5}$ cfu/ml) of virus (Corbeau et al., *Proc. Nat'l. Acad. Sci. USA* (1997), 93:14070–14075). However, the risk associated with the RCR virus evolved from co-transfection during HIV-1 vector preparation hinders its use as a gene transfer vector in healthy populations. Furthermore, there is no suitable animal model to demonstrate the safety of HIV-1 based vectors. To alleviate the safety concern of using HIV-1 vector for gene transfer in humans, lentiviral vectors derived from non-primate lentivirus has been described (Poeschla et al., *Nature Medicine* (1998), 4(3): 354–357; Olsen, *Gene Therapy* (1998), 5:1481–1487).

Simian Immunodeficiency Virus (SIV) exhibits cellular tropism similar to HIV-1, but it did not cause AIDS-like disease in humans who were accidentally infected with SIV (Rima et al., *New England J. Medicine* (1994), 330, 172–177–13; Khabbaz et al., *Lancet* (1992), 340:271–273). Recent reports suggested that SIV has broader co-receptor usage than HIV-1 (Chen et al., *J. Virology* (1997), 71: 2075–2714).

SUMMARY

For the purpose of enhanced safety, the SIV genome was used to develop a gene transfer vector system for quiescent cells and to demonstrate the safety of using SIV-based gene transfer system in the primate model. Another potential usefulness of the SIV gene transfer vector is to deliver anti-HIV molecules for gene therapy of AIDS. In this case, the anti-HIV molecules (for example, and without limitation, anti-sense RNA and ribozymes) will not be self-inhibitory of the packaging systems. Described herein is a stable SIV packaging cell line, which can produce high-titer of viral particles. High viral titers can be produced even after pseudotyping with heterologous viral envelope protein (s), including, without limitation, glycoprotein G derived from Vesicular Stomatitis Virus. The pseudotyped SIV vectors can transduce primary cells including monocyte-derived macrophage and peripheral blood lymphocytes effectively.

Accordingly, described herein is a safe and stable gene transfer system for human gene therapy. A method also is provided for generating high-titer helper cell line and an assay for detecting replication competent virus in retroviral particle production. In another embodiment, a retroviral vector is provided that can inhibit HIV-1 replication.

A packaging nucleic acid, for instance a plasmid and derivatives thereof are provided, comprising SIV gag, pol and accessory genes (vif, tat, rev), with or without env gene, but lacking a functional SIV packaging sequence (an approximately 40 base pair sequence located between 5' splicing donor site and initiation codon of gag). Also provided is a method for producing a stable packaging cell line by transferring the above-described packaging plasmid into a mammalian cell line, such as 293T or 293 cells.

A SIV transfer vector comprising cis-acting sequence for viral replication also is provided. One example includes the SIV 5'R and U5, about the first 320 base pair of the SIV gag coding sequence, the SIV rev-responding element (RRE) and the 3' LTR.

A method for producing retroviral particles by transfecting the above-described SIV packaging cell line with transfer vector also is provided. If no envelope is provided in the packaging nucleic acid, an envelope gene expression plasmid is co-transfected with the transfer vector. The envelope gene expression plasmid includes an envelope gene that may be derived from any enveloped virus, which includes, but is not limited to, amphotropic murine leukemia virus, Sendai virus, hepatitis viruses and vesicular stomatitis virus.

A method for testing for RCR virus in cell culture and a monkey model is provided as described herein.

A recombinant SIV retroviral transfer vector encoding anti-sense or ribozyme sequence of HIV (anti-HIV molecules) also is provided and is useful for producing anti-HIV virus particles by the above-described method for producing retroviral particles. The use of retrovirus according to any of the preceding for the treatment of any genetic and acquired diseases, also is provided.

Retrovirus particles prepared according to any of the preceding also may be used to deliver an immunogen of any infectious disease and tumor to cells for vaccination purpose.

BRIEF DESCRIPTION OF THE DRAWINGS

FIG. 2a. A PCR-generated fusion of CMV promoter and mRNA initiation site in SIV transfer construct pCRLacZ (SEQ ID NO: 1). b. PCR-generated sequence of SIV packaging construct with a deletion in the packaging sequence (SEQ ID NOS: 2–4).

DETAILED DESCRIPTION

Figure 1:
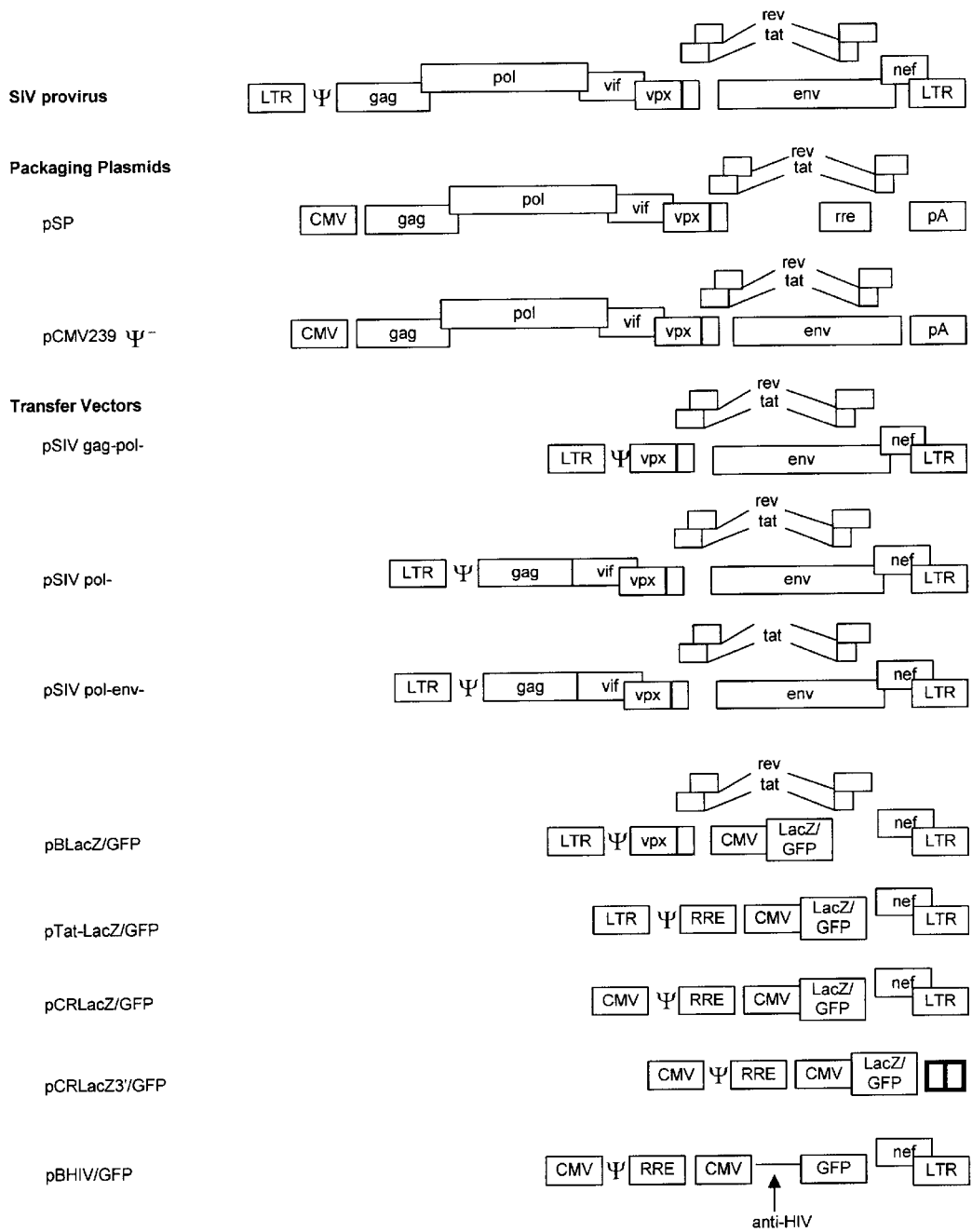
FIG. 1 is a schematic representation of SIV packaging and transfer plasmids described herein. CMV: cytomegalovirus early promoter; LTR: long terminal repeat; ψ: packaging sequence. RRE: rev response element. A filled portion of the 3' LTR of pCRLacZ3'/GFP indicates the deletion in U3 of that LTR.

Retroviruses are RNA viruses, which have a DNA intermediate that stably integrates into the host genome. Three major viral genes (gag, pol, and env) encode structural proteins, which are required for viral particle assembly. Specific (packaging) sequences on viral RNA genome are required for encapsidation of viral RNA into viral particles. The envelope protein of viral particles binds to specific receptor on the cell surface to initiate infection. Once the viral RNA enters the host, the RNA genome is converted to DNA and then integrates into the host chromosome. The integrated provirus then is transcribed, producing RNAs encoding viral proteins. The specific sequence (called packaging sequence) on the full-length, unspliced viral RNA can be recognized by viral core proteins and assemble into viral particles. The LTRs in the retrovirus genome are important for viral transcription, polyadenylation, replication, and integration of the provirus into the host genome. The LTR in the provirus has three regions that are defined functionally, U3, R, and U5. The U3 contains sequences important for transcription, including the enhancer, promoter and polyadenylation sites. R is the initiation and termination site of transcription. U5 contains the t-RNA binding site for reverse transcription.

Murine oncoretrovirus has been developed as gene transfer vector for delivering therapeutic genes into humans. However, this vector is prone to rearrange upon transducing into target cells. Cell division is also required for efficient gene transfer by murine retroviral vectors. Recently developed lentiviral vector based on Human Immunodeficiency Virus can overcome the dependence of cell division for transduction. However, the safety concern limits its use in humans. SIV can infect non-dividing cells as well as dividing cells and does not cause disease in humans. In one embodiment, a stable SIV packaging cell line is provided. Retroviral vectors encoding therapeutic genes can be produced by transfecting a transfer vector into a packaging cell line. The packaging cell line described herein typically includes all SIV genes under the transcriptional control of the cytomegalovirus early promoter. The SIV env gene may be omitted from the packaging cell line. Important cis-acting sequences (5' and 3' LTRs and packaging sequences) which are required for viral replication, are deleted in one embodiment of the packaging expression construct described herein (pSP). Clonal packaging cell lines were generated by electroporating pSP into 293T and 293 cells, respectively, and selected for neomycin (neo or G418) drug resistance. High-efficiency packaging cell lines were selected from 300 stable transfected cell lines by transfecting with transfer vector containing β-galactosidase gene (LacZ) or green fluorescent protein (GFP). The recombinant viruses were harvested from culture media and titered by standard methods used by those of skilled in the art. Gene rearrangement has been a common problem for growing large quantities of SIV constructs in *E. coli*. By establishing a stable SIV packaging cell line, there is no need to grow large quantities of expression construct (for example, plasmid DNA) for production of retroviral vectors.

A packaging nucleic acid is provided including, minimally, SIV gag and pol genes wherein the packaging sequence between the 5' splice site and the initiation site of the gag gene is removed. A desired sequence can be "removed" or "inactivated" by any method, including, without limitation, by deletion, substitution or insertion of nucleic acids to effectively disrupt the function of the desired sequence. For instance, for the packaging nucleic acid, the SIV packaging sequence can be removed by deletion, but also can be removed by any mutation that disrupts the ability of the packaging nucleic acid to be packaged in an SIV virus particle. As described below, the SIV packaging sequence can be removed from the SIV genome by deletion of sequences between the 5' splice site and the initiation site of the gag gene, for example, and without limitation, deletion of bases 1258 to 1297 of the reference SIV genome (GenBank Accession No. M33262). Inactivation of the 3' U3 region also is described below.

Similarly, a gene may be "inactivated" by insertion, deletion or substitution of nucleic acid sequences, resulting in failure of the gene to be expressed properly. Inactivation may be achieved by removal of regulatory sequences or by disruption of the protein's function, for instance by creation of a frameshift mutation in an open reading frame. In an example provided below, the env gene is inactivated by a frameshift mutation caused by the deletion of 97 nucleotides from the env sequence.

The packaging nucleic acid may be a substantially complete SIV genome with its packaging sequence removed. By "substantially complete" it is meant that the nucleic acid sequence contains all or most genetic elements found in the wild-type SIV, such as the reference SIV, so long as the modified SIV genome cannot be packaged, but provides the necessary genetic elements for packaging of the transfer vectors, the env gene being provided either by the packaging nucleic acid or by a nucleic acid, such as a plasmid, co-transfected with the transfer vector. Typically, one or both of the 3' LTR and the 5' LTR are removed from the packaging nucleic acid.

As described above, the env gene of the packaging nucleic acid may be functional, inactivated or removed or substituted with a different env gene. The packaging nucleic acid may contain a gene encoding an envelope gene derived from an enveloped virus other than SIV to pseudotype the recombinant virus. For example, and without limitation, the packaging nucleic acid may contain a gene encoding an envelope protein from amphotropic murine leukemia virus, Sendai virus, hepatitis viruses or vesicular stomatitis virus.

In use, the packaging nucleic acid is transfected into a mammalian cell, typically of a cell line, and cells are selected for the presence of the packaging nucleic acid, for instance by neo (G418) resistance when the packaging nucleic acid contains a neo gene. Once a transformed cell line is created, it can be transfected with a transfer vector to produce recombinant virus particles. Useful cell lines for the creation of a packaging cell line are 293 or 293T cells. Other cell lines may be transformed with the packaging nucleic acids, so long as the cells are sufficiently easily transfected, transformed and are capable of production of sufficiently high titers of recombinant retroviral particles, as are 293 cells. When the packaging vector does not contain an env gene, a nucleic acid, typically a plasmid, containing an env gene may be co-transfected with the transfer vector or otherwise introduced into the packaging cell line to complement the Packaging vector during production of recombinant virus particles.

As used herein, a "derivative" of a given nucleic acid is a nucleic acid having essentially the same sequence as the nucleic acid and that includes essentially the same genetic elements serving the same purpose as those genetic elements found in the original nucleic acid. A "derivative" of a given nucleic acid retains substantially identical expression characteristics of the nucleic acid. For instance, and without limitation, a derivative of a nucleic acid retains, where applicable, SIV-specific qualities (for instance, and without limitation, cell type-specific expression characteristics and cellular tropism), as compared to HIV-derived systems in retaining the essential safety features provided by use of SIV-derived vectors. Nucleic acid insertions, deletions and substitutions that do not alter the essential nature of the nucleic acid and genetic elements thereof fall within the definition of "derivatives." In reference to the packaging vectors and transfer vectors described herein, "derivatives" thereof include, without limitation: conservative nucleic acid additions, deletions or substitutions that do not affect substantially the ability of any genetic element to function as provided herein, such as the substitution of other promoters for the CMV promoter, the substitution of degenerate codons for other codons and conservative amino acid insertions, deletions and substitutions; the inclusion of different pseudotyping env proteins; modification or addition of restriction sites or recombination targets to facilitate cloning, for example, by insertion of a polylinker in the BglII site of the env gene in the transfer vectors; the addition of or modification of sequences to facilitate detection of or viral sequences or products thereof, such as by the addition of sequence or peptide (epitope) tags or PCR target sequences; substitution of all or part of the plasmid backbones of the plasmids described herein, including, without limitation, changing the antibiotic resistance, replication origin, and/or polylinker sequences, or by including additional functional or non-functional sequences, such as marker genes (such as LacZ or GFP) for any purpose.

A "genetic element" is any functional nucleic acid sequence or combination thereof, whether operating in cis or trans. "Genetic elements" include, without limitation: genes, promoters, polyadenylation (polyA) signal, enhancers, repressors, viral packaging sequences, signal sequences, RNA or protein splicing sites, recombination sequences and protein-binding sites. A typical minimal "gene" includes: 1) a promoter, 2) an "expressed sequence," which may be a protein coding sequence or a sequence encoding a desired RNA, for instance an anti-sense or catalytic RNA (ribozime), and 3) a polyA signal.

The transfer vectors include, in a 5' to 3' direction, 1) an SIV 5' LTR, or a modified version thereof in which all or part of the 5' LTR, typically including all or part of the U3 region is replaced by non-SIV promoter, or a derivative thereof; 2) an SIV packaging sequence or a derivative thereof; 3) an SIV rev-response element or a derivative thereof; 4) one of a non-SIV gene or a cloning site for insertion of a non-SIV gene; and 5) one of a 3' SIV LTR, a modified version thereof in which the U3 region is inactivated, or a derivative thereof. Non-SIV promoters can be virtually any mammalian promoter, and include, without limitation, the CMV and RSV promoters as well as tissue-specific promoters, such as those provided in Table 1, below.

TABLE 1

Tissue specific promoter/enhancer regulatory sequence.

platelet-derived growth factor-beta chain (PDGF-beta) promoter
woodchuck hepatitis virus post-transcriptional regulatory element (WPRE)
prostate specific antigen (PSA) promoter and/or enhancer
pancreatic amylase promoter
human VGF promoter
cardiac myosin light chain 2 (MLC-2v) promoter
alpha-1-antitrypsin promoter
hepatitis b promoter and enhancer
human insulin growth factor II promoter The transfer vector includes a cloning site for insertion of a gene to be transferred by the virus particles containing the packaged transfer vectors. The cloning site typically is a restriction endonuclease target sequence (restriction site), but may be a recombination site for targeted recombination by one of a number of methods for insertion of nucleic acid sequences into target sequences by recombination, such as, without limitation, Cre-Lox systems. The restriction site may be a native restriction site, such as the BglII site of the SIV env gene, as shown in Example 1, below, or a polylinker with multiple single-cut restriction sites in a short stretch of DNA. In use, the transfer vector contains a gene or genetic element, typically inserted into the cloning site, for expression in the target cell for the recombinant virus particle. As shown below, the gene may be an indicator gene such as LacZ and GFP, typically useful in determining transduction of a target cell population with the virus particles, or may be any gene or genetic element useful for, such as without limitation, therapeutic purposes for the delivery of a therapeutic gene, and for immune modulation purposes, such as for delivery of an antigen to a patient to elicit a desired immune response. Other uses for recombinant retrovirus viral particles are well-known, including transgenic technologies stem-cell genetic modification and bioengineering.

As used herein, the term "transfection" means the transfer of nucleic acid into a cell for expression of the nucleic acid in that cell. Transformation results from long-term expression of the transfected DNA in a cell line. Transfection methods include, without limitation, electroporation, liposome, viral-mediated, DEAE-dextran, calcium chloride and particle bombardment methods, among a variety of other methods. The creation of a stable "transformed" cell line typically involves transfection of the cell with a nucleic acid containing an antibiotic-resistance gene or other selectable marker to facilitate enrichment of transformed cells. "Transduction" means the infection and transfection of a cell with a virus particle, including a recombinant virus particle, which can result in the long-term transformation of the cell.

Two assays, one in vitro and other in vivo, were also developed for the detection of replication-competent virus. For the in vitro assay, CEMx174 cells, or other cells in which SIV can replicate, are infected with retroviral particles for one week and cell-free culture media is harvested to infect a second culture of CEMx174 cells for another week. From the second culture, the cell-free media is harvested and added to an indicator cell line sMAGI, which contains a single copy of LTR driven LacZ gene. Cells other than sMAGI cells may be used so long as they can be infected by replication-competent virus particles and contain an LTR-driven indicator gene. These cells are referred to herein as "RCV Indicator Cells." After three days incubation, the sMAGI cells are stained with X-gal solution. If there is any RCR present in the culture, it will activate the LTR-LacZ gene in infected cells. As a result, the transduced cells will appear blue. The total DNA isolated from the second CEMx174 cells culture also was subjected to PCR analysis of SIV sequence.

For the in vivo assay, rhesus monkeys are injected with retroviral particles and monitored for infectious SIV in peripheral blood lymphocytes (PBMC) at monthly intervals. The isolated PBMC are co-cultured with CEMx174 cells for one month. sMAGI cells are transduced with cell-free media harvested from the one-month co-culture. The DNA is extracted from the co-cultured CEMx174 cells and subjected to PCR analysis for SIV sequence. Both the in vitro and in vivo assays demonstrate that there is no replication competent virus (RCR) present in retroviral particles. As with the in vitro assay, the CEMx174 cells may be substituted with other cells in which SIV can replicate and the sMAGI cells may be replaced with other RCV indicator cells.

In another embodiment, a retroviral vector encoding an anti-HIV molecule is constructed. One example of this anti-HIV molecule is a 1500 base anti-sense sequence of HIV-1's vif, vpr, vpu, rev, tat, and env genes (nucleotides 5407–6833 of GenBank Accession No. K03455). These genes are absolutely required by HIV-1 for replication. By using large anti-sense sequence for targeted inhibition, varied subtypes of HIV-1 still can be inhibited in CD4 positive lymphocytes (Tung et al., *J. Med. Virol.* (1996), 48: 321–325, incorporated herein by reference).

Although specific DNA sequences are described in reference to the embodiments described herein, including specific sites at which the various nucleic acids are cut and ligated, inserted and deleted, these sites (for example, restriction sites and PCR primers) were chosen to facilitate the construction of the described nucleic acids. It is understood that the sites at which the various described nucleic acids are joined, inserted or deleted may vary so long as the desired function is substantially preserved. It is also understood that for each nucleic acid described herein, variants, analogs, alleles, conservative derivatives and homologues exist, or may be designed according to known parameters (for example, degenerate coding sequences or conservative amino acid substitutions may be introduced without substantially altering the structure and/or function of any element of the nucleic acid construct) and may be synthesized by any of a variety of known methods.

EXAMPLE 1

Construction of Packaging Vector pCMV293ψ⁻ and pSP

The SIV packaging vector (pSP) was constructed in three steps. First, a 9.5 Kb BsiEI-BsiEI fragment (nucleotides 721–10181 of GenBank Accession No. M33262 (SEQ ID NO: 5)) encoding all SIV proteins, but lacking the 5'U3, and 3' LTR, was isolated from full-length SIVmac molecular clone (239) and subcloned into eukaryotic expression vector Second, a 40 base-pairs packaging sequence (nucleotides 1258–1297 of GenBank Accession No. M33262) located between 5' splicing donor site and initiation codon of gag was deleted by PCR technique (FIG. 2a). In short, specific primers (5'-AGGCGCGCCTFTGTGTTGCACTTACCTGC-3' (SEQ ID NO: 6) and 5'-AGGCGCGCCTAGAGTGGGAGATGGGCGT-3' (SEQ ID NO: 7)) corresponding to either end of the deletion region were synthesized with an AscI restriction site on the 5'end. Together with other primers (5'-

TTTGGATCCAGTCGCTCTGCGGAGAGG-3' (SEQ ID NO: 8) and 5'-GAGACATCCCCAGAGCTGTTAG-3' (SEQ ID NO: 9), respectively), two DNA fragments were amplified, restricted with AscI and ligated in vitro. The ligated DNA was restricted with NarI and BamHI and used to replace NarI-BamHI fragment of wild-type SIVmac sequence in the backbone of pCDNA3.1+ to construct pCMV293ψ⁻. Third, a 99 bp PmlI to ClaI fragment (nucleotides 8233–8329 of GenBank Accession No. M33262) was also deleted to generate a frame-shift mutation in env gene to construct pSP (FIG. 1). It is understood that additional viral sequence may be deleted from SIV packaging construct so long as the deletion will not affect the packaging functions. Non-limiting examples of the viral sequences that may be deleted include tat, vif, rev, vpr, and vpx sequences.

EXAMPLE 2

Construction of Transfer Vectors

To construct the transfer vector, pSIV gag-pol⁻, a 4.2 KB Ava I fragment (nucleotides 1760–6010 of GenBank Accession No. M33262) was deleted from full-length SIV to construct a gag and pol deletion construct, which expresses env and other accessory genes (vpx, vpr, tat and rev). pSIVpol⁻ has a 754 bp deletion (3572–4325, BstEII fragment) in the pol gene of SIV genome. pSIV pol⁻env⁻ is a derivative of pSIVpol⁻ with a second deletion (8233–8329) in the env. For SIV transfer vectors with a marker gene, pBLacZ was constructed by inserting a 4 Kb DNA encoding LacZ expression cassette under the control of cytomegalovirus (CMV) early promoter into the BglII site of pSIV gag-pol⁻. pBGFP was constructed by inserting a 1.8 Kb DNA encoding green fluorescence gene (GFP) expression cassette into BglII site of pSIV gag-pol⁻. To construct ptat⁻LacZ, additional coding sequence (AvaI-XcmI fragment, 1760–7881 base pairs, encoding part of gag- pol, tat, vif vpx, vpr, rev) from pBLacZ is also deleted. The deletion of tat gene reduced the titer at least 100-fold. To further enhance the titer, the U3 region in the 5' LTR of ptat⁻LacZ was replaced with the CMV promoter (−626 to −10, relative to the transcriptional start site according to Boshart et al. (Cell (1985) 41:521–530) to construct pCR-Lac7 by PCR technique (FIG. 2b). In brief, a DNA fragment (616 base pairs) encoding CMV promoter was PCR amplified with primer FT66 (5'-TTTTGCATGCTTCGCGATGTACGGGCCAGAT-3' (SEQ ID NO: 10)) and FT67 (5'-AGAGAGCTCTGCTTATATAGACCT-3' (SEQ ID NO: 11)) from plasmid pCDNA3.1+. A DNA fragment (2330 base pairs) encoding SIV R to gag sequence was amplified with primer FT68 (5'-CTCTGTATTCAGTCGCTCTGC-3' (SEQ ID NO: 12)) and FT28 (5'-GAGACATCCCCAGAGCTGTTAG-3' (SEQ ID NO: 13)). These two PCR amplified DNA were treated with kinase and ligated with T4 DNA ligase. The ligated DNA was used as template for PCR with primer FT66 and FT28. The resulting DNA was cut with SphI and DraIII to isolate a 1.4 kb SphI-DraIII DNA fragment. This 1.4 kb SphI-DraIII DNA was used to replace the SphI-DraIII fragment (1–1632) in ptat⁻LacZ (FIG. 1). To construct a self-inactivating transfer vector (pCRLacZ3'), a 474 bp (9740–10213) was deleted from the 3' U3 region of LTR of pCRLacZ) by PCR methods with primers (5'-GCACTGTAATAAATCCCTTCC-3' (SEQ ID NO: 14) and 5'-CACTGCATTTCGCTCTGTATT-3' (SEQ ID NO: 15)) and pCRlacZ as template. The PCR amplified DNA was treated with kinase before self-ligation.

It is understood that additional modification can be made by those skilled in the art to delete or add additional nucleic acid sequence into SIV transfer vectors as long as the functional activity of transfer vectors are maintained. For example, internal CMV promoter can be replaced with different eukaryotic regulatory sequences; such as promoter and enhancer sequence derived from eukaryotic genome, which may function in particular tissue (tissue specific gene expression). Table 1 (above) provides examples of tissue specific regulatory sequences.

EXAMPLE 3

Creation of Stable SIV Packaging Cell Line

All cell lines were cultured in Dulbecco's-Modified-Eagle-Media (DMEM) supplemented with 10% fetal bovine serum and antibiotics. To generate an SIV packaging cell line, 293T or 293 cells were transfected with pCMV239 ψ⁻ or pSP and selected for G418 resistance (due to Neo gene in the pcDNA3.1+ vector). Individual Neo resistant (1 mg/ml) colonies were isolated and expanded into a cell line. Three hundred colonies were isolated and expanded into clonal cell lines. These cell lines were co-cultured with sMAGI for 48 hours and stained with X-gal. Positive clones showed blue color indicating the expression of SIV Tat gene, were selected for further analysis.

EXAMPLE 4

Titering of SIV Vectors

SIV vectors were prepared by co-transfecting transfer constructs with pCMV.VSVG, which expresses G protein of vesicular stomatitis virus into SIV packaging cells. Cell-free medium were harvested 72 hrs after transfection. An indicator cell line, sMAGI (Chackerian et al., Virology (1995), 213(2):386–94) was used for the transduction assay of SIV defective vectors (SIV gag-pol⁻ SIV pol⁻, SIV pol-env⁻). sMAGI cells are derived from the macaque mammary tumor cell and express human CD4 and encode an HIV LTR fused to the β-galactosidase (β-Gal) reporter gene. This cell line allows detection of productive infection of a single virus particle by exploiting the ability of the SIV Tat protein to trans-activate the β-Gal gene through the HIV LTR promoter. sMAGI cells were transduced with one ml of serial diluted viruses in the presence of 8 μg/ml of polybrene. Transduced cells were incubated for 3 days at 37° C. before X-gal staining. 293 cells were used for titering of SIV vectors with LacZ marker gene (Table 2, below). SIV vectors can also be made by co-transfecting with plasmid expressing different env gene for specific cell-type gene targeting. Examples of env genes include, but are not limited to amphotropic murine retrovirus, hepatitis virus, and other enveloped viruses. Furthermore, the envelope proteins can be modified to bind to specific target cells. The modification can be achieved by adding a ligand (or antibody) to specific receptor on the surface of target cells.

TABLE 2

Transduction efficiency of SIV vectors on 293 or sMAGI cells.

| Virus | Titer (TU/ml) |
|---|---|
| SIV gag-pol | $1 \times 10^7$ |
| SIVpol | $1 \times 10^7$ |
| SIVpol-env | $1 \times 10^7$ |
| BlacZ/GFP | $1 \times 10^7$ |

TABLE 2-continued

Transduction efficiency of SIV vectors on 293 or sMAGI cells.

| Virus | Titer (TU/ml) |
|---|---|
| Tat-BlacZ/GFP | $5 \times 10^4$ |
| CRLacZ | $3 \times 10^7$ |

T.U.: transducing unit.

EXAMPLE 5

Immunoprecipitation of SIV Packaging Cell Line

Figure 3:
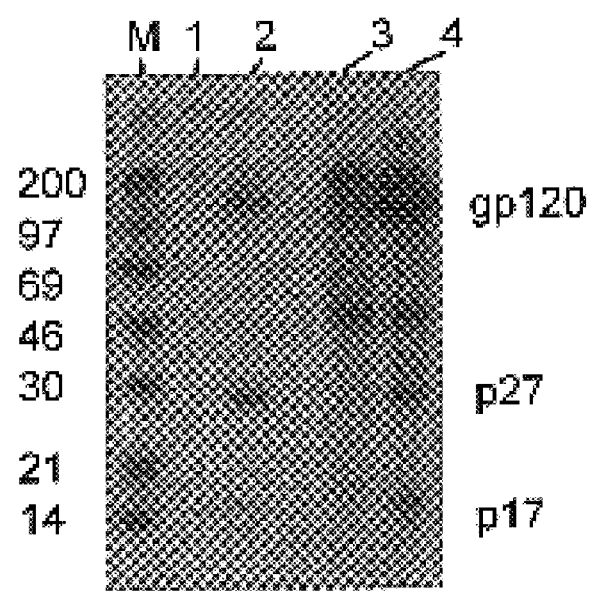
FIG. 3 Immunoprecipitation of pCMV239 ψ⁻ transfected 293T cells to demonstrate the viral protein expresion in the stable SIV packaging cell line. Lanes 1 and 3: mock transfected 293T cells. Lanes 2 and 4: pCMV239 ψ⁻ transfected 293T cells. 1 and 2: cell-free medium; 3 and 4: cell lysate. M: $^{14}$C labeled molecular weight marker.

Approximately $10^6$ SIV packaging cells were labeled with $^{35}S$ methionine for 16 hours. The cellular lysate and cell-free medium were immunoprecipitated with anti-SIV serum from infected animals. The precipitated viral proteins were analyzed by SDS gel electrophoresis (FIG. 3).

EXAMPLE 6

PCR Analysis of RCR in the SIV Vector Transduced Cells

Figure 4:
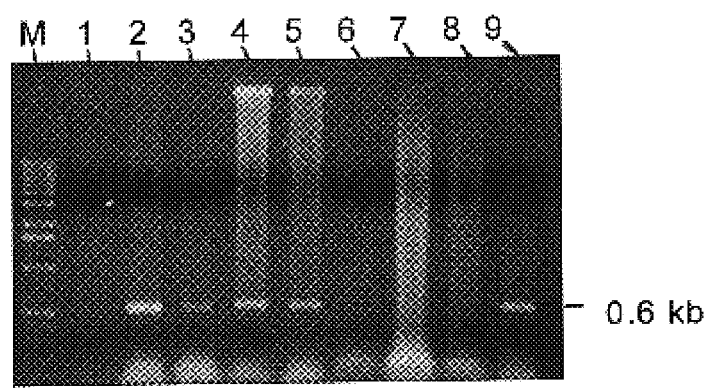
FIG. 4 PCR analysis of defective SIV vector transduced CEMx174 cells to demostrate the gene transfer into target cells and the lack of RCR in the transduced target cells. CEMx174 cells were transduced with VSV.G pseudotyped defective SIV (lanes 2–5) or cultured with second round cell-free medium (lanes 6–9). Lane 1: mock-transduced CEMx174 cells, lane 2 & 6: SIV gag-pol⁻/VSVG transduced, lane 3 & 7: SIV pol⁻/VSVG transduced, lanes 4 & 8: SIV pol⁻env⁻/VSVG transduced, lanes 5 & 9: full-length SIV transduced (positive control). A 0.6 kb band indicated the PCR product of R-Gag. M: 1 kb size (BRL/Life Science Tech.).

To monitor the presence of replication-competent virus in virus preparation, $10^5$ CEMx174 cells were transduced with 1 ml of cell-free SIV vectors ($10^6$ TU/ml). After one-week culture, the cell-free medium was harvested from the one-week culture of the transduced CEMx174 cells and used to culture CEMx174 cells again for another week. The total DNA was isolated from the first and second CEMx174 cell culture and subjected to a sensitive PCR analysis (FIG. 4). Specific primers FT33 and FT34 (5'-TTTGGATCCAGTCGCTCTGCGGAGAGG-3' (SEQ ID NO: 16) and 5'-ACAAGATCTAGTTTCTCACGCCCTACTCCCACT CT-3' (SEQ ID NO: 17)) derived from SIVmac were used to amplify a 600 bp fragment of R to the AUG of the gag gene (5' end of non-translating sequence in the transfer vector). The sensitivity of this PCR assay is less than 100 copies by using standard plasmid DNA as control. The positive results in the first culture indicate that defective SIV vectors transduce CEMx174 cells successfully (FIG. 4, lane 2–5). The negative results of PCR indicate the second culture was not infected with SIVmac (FIG. 4, lane 6–9). To avoid the false negative results, all sample DNAs were subjected to PCR for an endogenous β-globin gene and results were positive (data not shown). The results also indicate that there was no viral activity (cytopathic effect and p27) in the second culture even after 30 days incubation (the last day monitored). Viral activity was detected in wild-type full-length virus infected control cells after 5 days culture.

EXAMPLE 7

Transduction of Macrophage and Peripheral Blood Lymphocytes

Human peripheral blood lymphocytes were collected from healthy donors and cultured in RPMIx1740 with 10% fetal bovine serum. After 24-hour incubation in cell culture dish, adherent macrophages were separated from suspension lymphocytes. Both macrophage and lymphocyte cultures were incubated with SIV vectors with Lac Z marker gene for 24 hours. The transduced cells then stained with X-Gal 72 hrs later. The results indicate that both macrophage and primary lymphocyte can be easily transduced with SIV vector.

EXAMPLE 8

Figure 5:
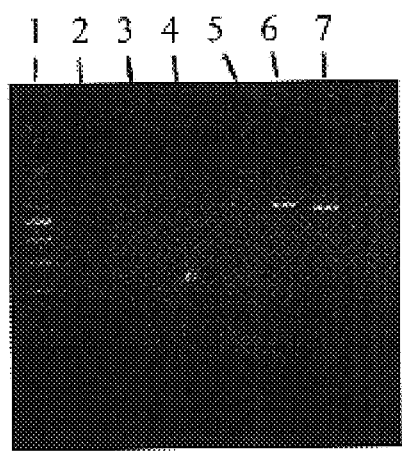
FIG. 5 PCR Analysis of PBMC co-cultured with CEMx174 Cells to demonstrate there is no RCR in monkeys that received SIV particles. Lane 1: Size marker (100 bp ladder, New England Biolabs), lane 2–5: PBMC from SIV gag⁻pol⁻ inoculated monkeys at 2 and 8 months post inoculation, lane 6: SIV infected, lane 7: positive control of 1 ng plasmid DNA. A 600 bp band indicates SIV LTR sequence.

Monitoring of Replication Competent Virus in rhesus Monkeys Inoculated with SIV Vectors To address safety issue of SIV vector in future clinical trials, the most sensitive assay was used; inoculating SIV vector (SIV gag⁻pol⁻) into rhesus monkeys and monitoring the replication competent virus. The vector without the marker gene was used to avoid the potential problem of immune mediated elimination (of β-galactosidase). Two rhesus monkeys were inoculated with SIV gag⁻pol⁻ ($10^7$ pfu) through intramuscular and subcutaneous routes three times at two-week intervals. Peripheral blood lymphocytes (PBMC) were collected at monthly intervals. PBMC ($3 \times 10^6$) were used for co-culture with CEMx174 cells for up to 30 days. DNA was extracted from co-culture cells and subjected to PCR analyses (FIG. 5). The PBMC from SIV persistently infected animals was used as positive controls. The results showed that no SIV is detected in animals inoculated with SIV gag⁻pol⁻ at any time points (up to 11 months) by PCR or co-culture. Control animals showed positive results by PCR and co-culture. The two animals inoculated with SIV gag⁻pol⁻ are still healthy and have no sign of SIV infection one-year after inoculation. SIV infection usually develops disease within 6 months. This experiment demonstrated the safety of using SIV vectors in future clinical trails.

The above-described experiments show the utility of a safe SIV packaging cell line for gene transfer in humans. Practically, this gene transfer system can be used to deliver any therapeutic gene into any target cells in humans. Although the invention has been described with the reference to the preferred embodiment, it is understood that modifications can be made by anyone, who is familiar with the skills in the art.

I claim:

1. A method of producing retroviral particles by transfecting with an SIV transfer vector an SIV packaging cell line comprising a nucleic acid comprising an SIV 5' splice donor site 5' to SIV gag and pol genes, wherein the packaging sequence between the 5' splice donor site and the initiation site of the gag gene is removed.

2. The method of claim 1, the transfer vector comprising, in a 5' to 3' direction:

a. an SIV 5' LTR, or a modified version thereof in which all or part of the U3 region of the 5' LTR is replaced by a non-SIV promoter, or a derivative thereof;

b. an SIV packaging sequence or a derivative thereof;

c. an SIV rev-response element or a derivative thereof;

27 d. one of a gene or a cloning site for insertion of a non-SIV gene; and e. one of a 3' SIV LTR, a modified version thereof in which the U3 region is inactivated, or a derivative thereof.

3. The method of claim 1 wherein the nucleic acid is one of pSP, or a derivative thereof, and pCMV239 ψ⁻, or a derivative thereof.

4. An isolated nucleic acid for use in producing a SIV packaging cell line comprising an SIV 5' splice donor site 5' to SIV gag and pol genes, or derivatives thereof, wherein the packaging sequence between the 5' splice donor site and the initiation site of the gag gene is removed.

5. The nucleic acid of claim 4, comprising a substantially complete SIV genome in which said packaging sequence is removed.

6. The nucleic acid of claim 5, in which about a 40 base deletion is made between said 5' splice site and said initiation site of the gag gene.

7. The nucleic acid of claim 5, in which said SIV genome is that of SEQ ID NO: 5, bases 1258 to 1297 of which are deleted.

8. The nucleic acid of claim 5, in which at least one of a 5' LTR and a 3' LTR are removed from said SIV genome.

9. The nucleic acid of claim 5, in which said env gene is inactivated.

10. The nucleic acid of claim 9, in which said env gene is inactivated by a frameshift mutation.

11. The nucleic acid of claim 10, in which said SIV genome is that of SEQ ID NO: 5 from which nucleotides 8233 to 8329 are deleted to cause said frameshift mutation.

12. The nucleic acid of claim 4, comprising an SIV envelope gene.

13. The nucleic acid of claim 4, comprising an envelope gene derived from an enveloped virus other than SIV.

14. The nucleic acid of claim 13, wherein said enveloped virus is selected from the group consisting of amphotropic murine leukemia virus, Sendai virus, hepatitis viruses and vesicular stomatitis virus.

15. The nucleic acid of claim 14, wherein said envelope gene is vesicular stomatitis virus glycoprotein G.

16. A cell comprising the nucleic acid of claim 4.

17. The cell of claim 16, wherein said nucleic acid is pSP or a derivative thereof.

18. The cell of claim 17, wherein said nucleic acid is pSP.

19. The cell of claim 16, wherein said nucleic acid is pCMV239 ψ⁻ or a derivative thereof.

20. The cell of claim 16, wherein said nucleic acid is pCMV239 ψ⁻.

21. A cell line comprising said cell of claim 16.

22. An isolated and purified nucleic acid consisting of one of plasmid pSP, or a derivative thereof.

23. The nucleic acid of claim 22, consisting of plasmid pSP.

24. An isolated and purified nucleic acid consisting of one of plasmid pCMV239 ψ⁻, or a derivative thereof.

25. The nucleic acid of claim 24, consisting of plasmid pCMV239 ψ⁻.

26. An SIV transfer vector, comprising:

a. an SIV 5' LTR, or a modified version thereof in which all or part of the U3 region of the 5' LTR is replaced by a non-SIV promoter, or a derivative thereof;

b. an SIV packaging sequence or a derivative thereof;

c. an SIV rev-response element or a derivative thereof;

d. one of a gene or a cloning site; and e. one of a 3' SIV LTR, a modified version thereof in which a U3 region is inactivated, or a derivative thereof.

28

27. The transfer vector of claim 26, wherein said non-SIV promoter is the CMV promoter.

28. The transfer vector of claim 26, wherein said 3' LTR is modified such that said U3 region is inactivated.

29. The transfer vector of claim 26, comprising, in a 5' to 3' direction a nucleic acid consisting of:

a. an SIV 5' LTR;

b. an SIV packaging sequence;

c. an SIV rev-response element;

d. a cloning site; and e. a 3' SIV LTR.

30. The transfer vector of claim 26, comprising, in a 5' to 3' direction:

a. a modified SIV 5' LTR in which all or part of said U3 region of said 5' LTR is replaced by a non-SIV promoter, or a derivative thereof;

b. an SIV packaging sequence or a derivative thereof;

c. a rev-response element or a derivative thereof;

d. one of a gene or a cloning site; and e. a 3' SIV LTR or a derivative thereof.

31. The transfer vector of claim 30, wherein the non-SIV promoter is a CMV promoter.

32. The transfer vector of claim 26, comprising:

a. only about the first 320 base pairs of gag coding sequence; and b. said 3' SIV LTR.

33. The transfer vector of claim 26, comprising one of pBLacZ, pBGFP, substituted versions thereof and a derivative thereof.

34. The transfer vector of claim 33, consisting of one of plasmid pBLacZ, a substituted version thereof and a derivative thereof.

35. The transfer vector of claim 33, consisting of plasmid pBLacZ.

36. The transfer vector of claim 33, consisting of one of plasmid pBGFP, a substituted version thereof and a derivative thereof.

37. The transfer vector of claim 33, consisting of plasmid pBGFP.

38. The transfer vector of claim 26, comprising one of pTat-LacZ, pTat-GFP, substituted versions thereof or a derivative thereof.

39. The transfer vector of claim 38, consisting of one of plasmid pTat-LacZ, a substituted version thereof and a derivative thereof.

40. The transfer vector of claim 38, consisting of plasmid pTat-LacZ.

41. The transfer vector of claim 38, consisting of one of plasmid pTat-GFP, a substituted version thereof and a derivative thereof.

42. The transfer vector of claim 38, consisting of plasmid pTat-GFP.

43. The transfer vector of claim 26, comprising one of pCRLacZ3', pCRGFP3', substituted versions thereof or a derivative thereof.

44. The transfer vector of claim 43, consisting of one of plasmid pCRLacZ3', a substituted version thereof and a derivative thereof.

45. The transfer vector of claim 43, consisting of one of plasmid pCRLacZ3'.

46. The transfer vector of claim 43, consisting of one of plasmid pCRGFP3', a substituted version thereof and a derivative thereof.

47. The transfer vector of claim 43, consisting of plasmid pCRGFP3'.

48. The transfer vector of claim 26, comprising pBHIV/GFP, substituted versions thereof or a derivative thereof.

49. The transfer vector of claim 48, consisting of plasmid pBHIV/GFP.

50. The transfer vector of claim 26, comprising pSIVgag$^-$pol$^-$, substituted versions thereof and a derivative thereof.

51. The transfer vector of claim 50, consisting of plasmid pSIVgag$^-$pol$^-$.

52. The transfer vector of claim 26, comprising pSIVpol$^-$, substituted versions thereof and a derivative thereof.

53. The transfer vector of claim 52, consisting of plasmid pSIVpol$^-$.

54. The transfer vector of claim 26, comprising pSIVpol$^-$env$^-$, substituted versions thereof and a derivative thereof.

55. The transfer vector of claim 54, consisting of plasmid pSIVpol$^-$env$^-$.

56. The transfer vector of claim 26, comprising a gene encoding an anti-HIV molecule selected from the group consisting of an anti-sense nucleic acid and a ribozyme.

57. A recombinant virus particle comprising the SIV transfer vector of claim 26.

58. A method of producing a stable SIV packaging cell line comprising the step of transfecting the a mammalian cell line with the nucleic acid of claim 4.

59. The method of claim 58, wherein the nucleic acid is one of pSP, or a derivative thereof, and pCMV239 ψ$^-$, or a derivative thereof.

60. The method of claim 58, wherein the nucleic acid is pSP or a derivative thereof.

61. The method of claim 60, wherein the nucleic acid is pSP.

62. The method of claim 58, wherein the nucleic acid is pCMV239 ψ$^-$ or a derivative thereof.

63. The method of claim 62, wherein the nucleic acid is pCMV239 ψ$^-$.

64. The method of claim 58, wherein said a mammalian cell line is one of a 293T and a 293 cell.

65. A method for testing for replication-competent SIV virus or recombinant versions thereof, comprising the steps of:
   a. inoculating a non-human primate with recombinant SIV virus particles to be tested;
   b. collecting peripheral blood lymphocytes from the non-human primate;
   c. co-culturing the peripheral blood lymphocytes with cells in which SIV can replicate;
      i) testing the co-culture for replication-competent virus by at least one of 1) incubating replication-competent virus indicator cells with cell-free supernatant from the co-culture and staining the sMAGI cells for LacZ expression, and
      ii) analyzing DNA extracted from the co-culture for the presence of SIV-specific nucleic acid sequences.

66. The method of claim 65, wherein the method for analyzing the DNA is a PCR method.

67. The method of claim 65, wherein the cells in which SIV can replicate are CEMx174 cells.

68. The method of claim 65, wherein the replication-competent virus indicator cells are sMAGI cells.

69. A method for testing for replication-competent SIV virus or recombinant versions thereof, comprising the steps of:
   a. culturing the virus with a first culture of cells in which SIV can replicate;
   b. inoculating a second culture of cells in which SIV can replicate with cell-free supernatant of the first culture; and
   c. testing the second culture for replication-competent virus by at least one of
      i) incubating replication-competent virus cells with cell-free supernatant from the second culture and staining the replication-competent virus indicator cells for LacZ expression; and
      ii) analyzing DNA extracted from cells of the second culture for the presence of SIV-specific nucleic acids.

70. The method of claim 69, wherein the cells in which SIV can replicate are CEMx174 cells.

71. The method of claim 69, wherein the replication-competent virus indicator cells are sMAGI cells.

\* \* \* \* \*